(12) United States Patent
Bussat et al.

(10) Patent No.: US 12,070,512 B2
(45) Date of Patent: *Aug. 27, 2024

(54) TARGETED GAS-FILLED MICROVESICLES FORMULATION

(71) Applicant: Bracco Suisse SA, Cadempino (CH)

(72) Inventors: Philippe Bussat, Pers-Jussy (FR); Anne Lassus, Carouge (CH)

(73) Assignee: Bracco Suisse SA, Cadempino (CH)

( * ) Notice: Subject to any disclaimer, the term of this patent is extended or adjusted under 35 U.S.C. 154(b) by 238 days.

This patent is subject to a terminal disclaimer.

(21) Appl. No.: 17/352,773

(22) Filed: Jun. 21, 2021

(65) Prior Publication Data

US 2021/0386872 A1 Dec. 16, 2021

Related U.S. Application Data

(63) Continuation of application No. 16/867,685, filed on May 6, 2020, now Pat. No. 11,071,792, which is a continuation of application No. 15/536,393, filed as application No. PCT/EP2015/080199 on Dec. 17, 2015, now Pat. No. 10,682,429.

(30) Foreign Application Priority Data

Dec. 18, 2014 (EP) ..................................... 14199057

(51) Int. Cl.
*A61K 49/22* (2006.01)
*A61B 8/08* (2006.01)

(52) U.S. Cl.
CPC ............ *A61K 49/223* (2013.01); *A61B 8/481* (2013.01)

(58) Field of Classification Search
CPC .............................. A61K 49/223; A61B 8/481
See application file for complete search history.

(56) References Cited

U.S. PATENT DOCUMENTS

| | | |
|---|---|---|
| 5,271,928 A | 12/1993 | Schneider et al. |
| 5,413,774 A | 5/1995 | Schneider et al. |
| 5,445,813 A | 8/1995 | Schneider et al. |
| 5,556,610 A | 9/1996 | Yan et al. |
| 5,597,549 A | 1/1997 | Schneider et al. |
| 5,827,504 A | 10/1998 | Yan et al. |
| 7,794,693 B2 | 9/2010 | Bussat et al. |
| 9,381,258 B2 | 7/2016 | Bussat et al. |
| 2008/0107607 A1 | 5/2008 | Bussat et al. |
| 2013/0156706 A1 | 6/2013 | Bettinger et al. |

FOREIGN PATENT DOCUMENTS

| | | |
|---|---|---|
| EP | 0554213 A1 | 8/1993 |
| WO | WO1994-009829 A1 | 5/1994 |
| WO | WO1997-029783 A1 | 8/1997 |
| WO | WO2003-074005 A2 | 9/2003 |
| WO | WO2003-084574 A1 | 10/2003 |
| WO | WO2004-069284 A2 | 8/2004 |
| WO | WO2007-067979 A2 | 6/2007 |

OTHER PUBLICATIONS

Huang et al., J. Pharm. Sci., 2001, 90(12), p. 1917-1926. (Year: 2001).*
Karow, Anne R. et al., "Buffer Capacity of Biologics—From Buffer Salts to Buffering by Antibodies", Biotechnology Progress, 2013, vol. 29, No. 2, pp. 480-492, XP002712421, ISSN: 8756-7938, DOI: 10.1002/BTPR.1682, American Institute of Chemical Engineers.
Pillai, R. et al., "A Phospholipid-PEG2000 Conjugate of a Vascular Endothelial Growth Factor Receptor 2 (VEGFR2)—Targeting Heterodimer Peptide for Contrast-Enhanced Ultrasound Imaging of Angiogenesis", Bioconjugate Chemistry, 2010, vol. 21, No. 3, pp. 556-562, XP055195751, ISSN: 1043-1802, DOI; 10.1021/bc9005688.
Santana, Hector et al, "Screening for stability and compatibility conditions of recombinant human epidermal growth factor for parenteral formulation: Effect of pH, buffers, and excipients", International Journal of Pharmaceutics, vol. 452, No. 1, 2013, pp. 52-62, XP028573215, ISSN: 0378-5173, DOI: 10.1016/J. IJPHARM. 2013, Elsevier BV, NL.
European Search Report for European application No. EP14199057. 2, mail date Jul. 7, 2015.
International Search Report and Written Opinion for PCT application No. PCT/EP2015/080199, mail date Mar. 24, 2016.

\* cited by examiner

*Primary Examiner* — Michael G. Hartley
*Assistant Examiner* — Leah H Schlientz
(74) *Attorney, Agent, or Firm* — VIVICAR Law, PLLC

(57) ABSTRACT

Suspension of gas-filled microvesicles comprising a targeting ligand for binding to KDR or VEGF/KDR complex. The suspension is obtained by reconstituting a freeze-dried residue with a carbohydrate-containing solution in the presence of a physiologically acceptable gas and is stabilized by the presence of histidine.

17 Claims, No Drawings

Specification includes a Sequence Listing.

SEQUENCE LISTING

```
<160> NUMBER OF SEQ ID NOS: 2

<210> SEQ ID NO 1
<211> LENGTH: 22
<212> TYPE: PRT
<213> ORGANISM: artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (6)..(13)

<400> SEQUENCE: 1

Ala Gly Pro Thr Trp Cys Glu Asp Asp Trp Tyr Tyr Cys Trp Leu Phe
1               5                   10                  15

Gly Thr Gly Gly Gly Lys
            20

<210> SEQ ID NO 2
<211> LENGTH: 21
<212> TYPE: PRT
<213> ORGANISM: artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION,
<220> FEATURE:
<221> NAME/KEY: DISULFID
<222> LOCATION: (2)..(12)

<400> SEQUENCE: 2

Val Cys Trp Glu Asp Ser Trp Gly Gly Glu Val Cys Phe Arg Tyr Asp
1               5                   10                  15

Pro Gly Gly Gly Lys
            20
```

TARGETED GAS-FILLED MICROVESICLES FORMULATION

CROSS-REFERENCE TO RELATED APPLICATIONS

This application is a continuation of U.S. application Ser. No. 16/867,685, filed May 6, 2020, which is a continuation of U.S. application Ser. No. 15/536,393, filed Jun. 15, 2017, which is the national stage application of corresponding International Application Number PCT/EP2015/080199, filed Dec. 17, 2015, which claims priority to and the benefit of European Application Number EP14199057.2, filed Dec. 18, 2014, all of which are hereby incorporated by reference in their entirety.

TECHNICAL FIELD

The invention relates to a suspension of targeted gas-filled microvesicles, to a formulation for the preparation thereof and to its use as diagnostic agent.

BACKGROUND OF THE INVENTION

Rapid development of contrast agents in the recent years has generated a number of different compositions and formulations, which are useful in contrast-enhanced imaging of organs and tissues of human or animal body as well as in therapeutic treatments thereof.

A class of contrast agents, particularly useful for ultrasound contrast imaging, includes suspensions of gas bubbles of nano- and/or micro-metric size dispersed in an aqueous medium. The gas is typically entrapped or encapsulated in a stabilizing film layer comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles").

Of particular interest are aqueous suspensions of gas-filled microvesicles where the bubbles of gas are bounded at the gas/liquid interface by a very thin envelope (film) involving a stabilizing amphiphilic material (typically a phospholipid) disposed at the gas to liquid interface. Examples of aqueous suspension of gas-filled microvesicles and preparation thereof are disclosed, for instance, in U.S. Pat. Nos. 5,271,928, 5,445,813, 5,413,774, 5,556,610, 5,597,549, 5,827,504, WO 97/29783 and WO2004/069284.

More recently, attention has been given to so-called "molecular imaging", where suitable target-specific components are used in the formulation of the contrast agents, for allowing selective contrast-enhanced imaging of organs or tissues. Examples of targeting ligands include, for instance, peptides, proteins, antibodies, aptamers or carbohydrates capable of binding to specific receptors expressed by organs or tissues during pathogenic processes such as, for instance, angiogenesis, inflammation or thrombus formation.

For instance, International Patent applications WO 03/74005, WO 03/084574 and WO 2007/067979 describe suitable peptides which selectively target receptors in vulnerable plaques and tumor specific receptors, such as kinase domain region (KDR) and VEGF (vascular endothelial growth factor)/KDR complex. As described in these patent applications, such peptides are used for formulating target-specific gas-filled microvesicles suitable for binding to KDR or VEGF/KDR complex.

Gas-filled microvesicles are typically prepared by suspending a solid formulation (e.g. in the form of a powdered residue, prepared for instance by freeze-drying) into a physiologically acceptable aqueous solution, in the presence of a physiologically acceptable gas. The obtained suspension of gas-filled microvesicles may then be administered, typically by (intravenous) injection.

As observed by the Applicant, the suspension of the solid formulation in the aqueous solution (also referred to the art as "reconstitution of the dry residue) may represent a critical step of the preparation process of the microvesicles, and many parameters of the suspension step (including for instance the type of isotonic agent and its pH) may affect the characteristics of the microvesicles in the final suspensions.

The Applicant has now found that histidine is particularly useful as pH-adjusting agent for preparing suspensions of peptide-containing gas-filled microvesicles in a carbohydrate-containing physiologically acceptable aqueous solution.

SUMMARY OF THE INVENTION

An aspect of the invention relates to an aqueous suspension of gas-filled microvesicles, said microvesicles comprising a phospholipid and a targeting ligand comprising a peptide having an amino acid sequence selected from AGPTWCEDDWYYCWLFGTGGGK (SEQ ID NO: 01), VCWEDSWGGEVCFRYDPGGGK (SEQ ID NO: 02) or a combination thereof, said suspension further comprising a carbohydrate and histidine.

Preferably said microvesicle further comprises a fatty acid.

Preferably, the targeting ligand is in the form of a dimeric peptide comprising a combination of both SEQ ID NO: 01 and SEQ ID NO: 02.

More preferably said dimeric peptide has the following formula I:
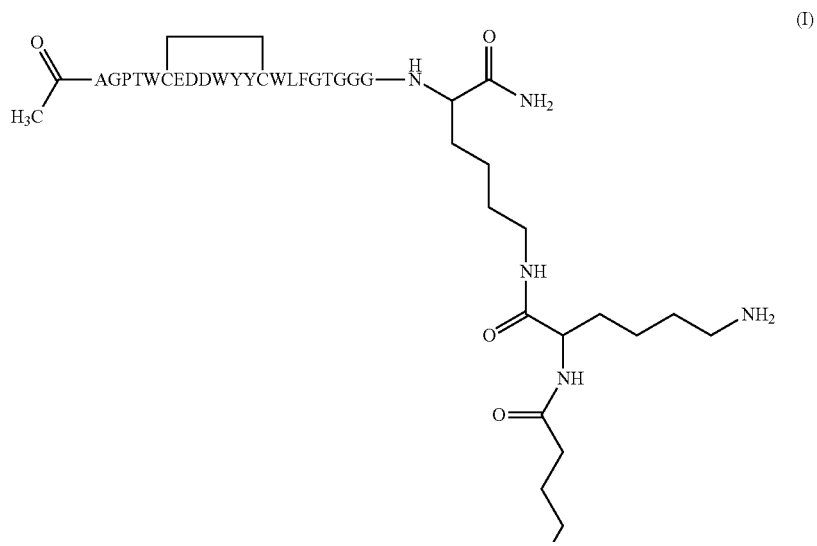
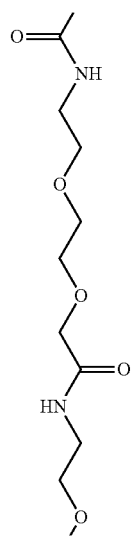
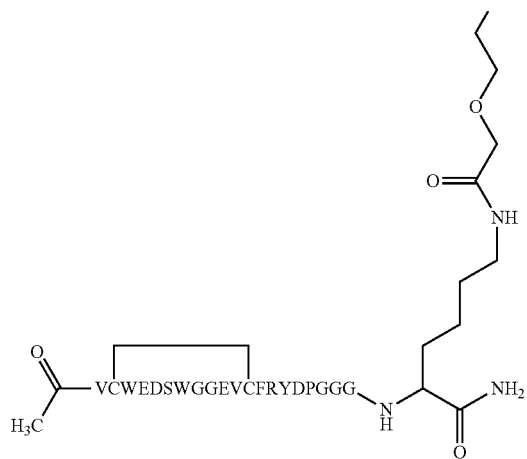
(I)

In a preferred embodiment the targeting ligand is covalently bound to a phospholipid, preferably a pegylated phospholipid.
Particularly preferred is a targeting ligand in the form of a lipopeptide of formula (II):
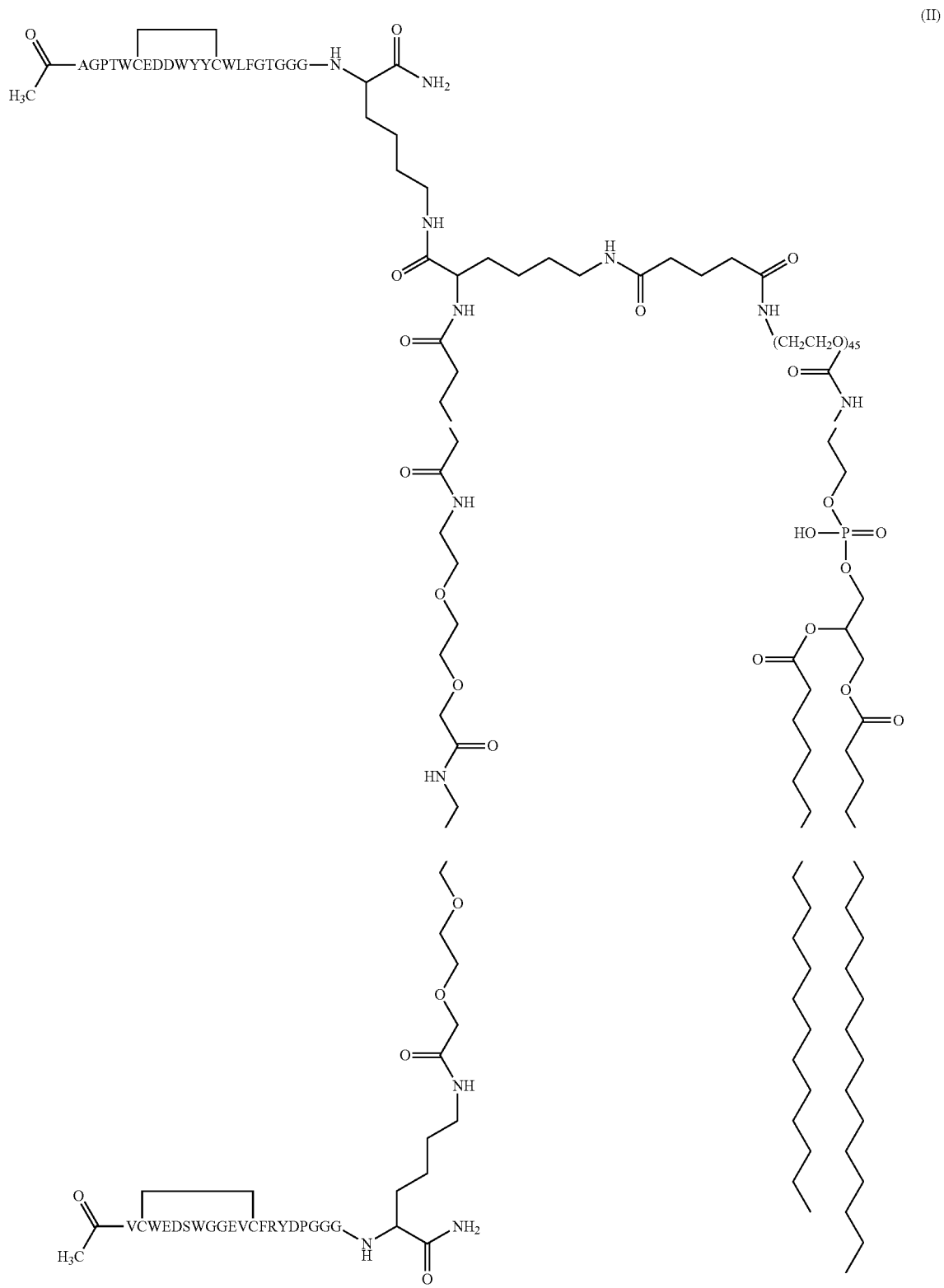
(II)

Preferably the carbohydrate is glucose, sucrose or mannitol, more preferably glucose Another aspect of the invention relates to a freeze-dried precursor formulation for preparing a suspension of gas-filled microvesicles comprising:

a phospholipid, a targeting ligand, histidine, optionally a fatty acid, optionally a pegylated phospholipid and a lyophilizing agent.

Another aspect of the invention relates to a pharmaceutical kit comprising:

(a) a freeze-dried precursor formulation as defined above; and (b) a carbohydrate-containing aqueous solution, for reconstituting said precursor.

DETAILED DESCRIPTION OF THE INVENTION

An aqueous suspension of gas-filled microvesicles may typically be prepared by suspending a freeze-dried precursor formulation (containing the relevant component for forming the gas-filled microvesicle) in a physiologically acceptable vehicle in the presence of a suitable gas. In general, it is preferable for the injected solution to be iso-osmolar, such that its osmolality lies within the physiological range of osmolality of blood, typically between 285 and 310 mOsmol per kg. As known in the art, the osmolality of a real solution corresponds to the molality of an ideal solution containing nondissociating solutes and is expressed in osmoles or milliosmoles per kilogram of solvent (Osmol per kg or mOsmol per kg, respectively).

Typically, iso-osmolar saline (e.g. NaCl) solutions are the first choice of aqueous vehicle for reconstituting the dry formulation to obtain the desired suspension of microvesicles for injection. As observed by the Applicant, saline vehicles (or more in general electrolytes-containing vehicles) shall however preferably be avoided for the preparation of microvesicles containing certain targeting peptides, in particular those comprising amino acid sequences illustrated above. Such peptide-containing gas-filled microvesicles, formed upon suspension with a saline vehicle, may in fact tend to aggregate to each other to form more or less stable aggregates which may then reduce the efficacy of the preparation and possibly cause safety issues, e.g. if the size of the aggregates is too large.

To limit such aggregation phenomena, alternative liquids may thus be used for suspending the dry formulations, such as commercially available carbohydrate solutions.

Commercial aqueous carbohydrate solutions for injection (e.g. mannitol, sucrose or glucose solutions) may however show variable pH values. For instance, commercial 5% glucose solutions for injection may have pH values ranging from about 3.2 to about 6.5. In the present description and claims, where not differently specified, the term "glucose" refers to the natural occurring enantiomer "D-glucose", also known as "dextrose".

The Applicant has now observed that formulations containing targeting peptides, and in particular the KDR-binding peptides listed above, show a substantial variability in the final characteristics of the microvesicles suspension when dispersed into carbohydrate (and particularly glucose) solutions at different pH values. In particular it has been observed that while the reconstitution of dry formulations with solutions at a pH of about 6.5 provides suspensions with a relatively high number of microvesicles, when the same dry formulation is reconstituted with solutions at lower pH the number of microvesicles in the suspension may be reduced.

To avoid the negative effects of such low pH values in the final suspension, pH adjusting agents may be used, in order to allow the reconstitution of the dry residue to take place at a suitably pH (typically from about 6 to about 8.5, preferably from about 7 to about 8). The Applicant has however observed that most of the conventional pH adjusting agents show a certain number of drawbacks within the usual ranges of pH of carbohydrate solutions for injection.

For instance, alkalinizing agents, such as sodium bicarbonate, shall be added in relatively high concentration to the suspension when the dispersing solution has a relatively low pH, in order to allow an optimal redispersion of the formed microvesicles. On the other side, if the pH value of the dispersing solution is relatively high, such high concentrations of alkalinizing agent would result in too high pH values in the final suspension which are incompatible with intravenous injection of the suspension.

Conventional buffering agents, such as Tris/HCl buffer or phosphate buffer shall be added at relatively high concentrations to obtain the desired pH adjusting effect in the whole range of microvesicles preparations; however it has been observed that such high concentrations may determine undesirable drawbacks in the preparation process of the microvesicles, with consequent possible negative effects on the characteristics of the microvesicles in the final suspension.

Contrary to the negative effects of the above pH adjusting agents, the Applicant has now found that histidine provides acceptable suspensions of gas-filled microvesicles upon redispersion of different dry residues having variable formulations (in particular with different amounts of targeting peptides) within the typical range of pH values of commercially available carbohydrate dispersing solutions. In addition, it has been observed that histidine may be used within a relatively large concentration range, without negatively affecting the properties of the final suspension of microvesicles.

The liquid suspension of gas-filled microvesicles according to the invention may typically be prepared by dissolving a phospholipid-containing formulation in an aqueous carrier. The formulation thus comprises a phospholipid optionally in combination with additional amphiphilic materials (e.g. fatty acids); the targeting peptide is preferably present in the formulation as a lipopeptide (i.e. peptide covalently bound to a phospholipid). The formulation is typically in the form of a freeze-dried (lyophilized) formulation, preferably comprising lyophilization additives. The gas-filled microvesicles of the invention can be prepared by admixing (or reconstituting) said formulation with the physiologically acceptable liquid carrier in the presence of a physiologically acceptable gas.

Phospholipids

As used herein, the term "phospholipid" is intended to encompass amphiphilic compounds containing at least one phosphate group and at least one, preferably two, ($C_{12}$-$C_{24}$) hydrocarbon chain, capable of forming a stabilizing film-layer (typically in the form of a mono-molecular layer) at the gas-water boundary interface in the final microbubbles suspension. Accordingly, these materials are also referred to in the art as "film-forming phospholipids".

The term phospholipids includes naturally occurring, semisynthetic or synthetic products, which can be employed either singularly or as mixtures.

Examples of suitable phospholipids include esters of glycerol with one or preferably two (equal or different)

residues of fatty acids and with phosphoric acid, wherein the phosphoric acid residue is in turn bound to a hydrophilic group such as, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids diesters of phosphatidylcholine, ethylphosphatidylcholine, phosphatidylglycerol, phosphatidic acid, phosphatidylethanolamine, phosphatidylserine, phosphatidylinositol or of sphingomyelin.

Specific examples of phospholipids are, for instance, dilauroyl-phosphatidyl-choline (DLPC), dimyristoyl-phosphatidylcholine (DMPC), dipalmitoyl-phosphatidyl-choline (DPPC), diarachidoyl-phosphatidylcholine (DAPC), distearoyl-phosphatidyl-choline (DSPC), dioleoyl-phosphatidylcholine (DOPC), 1,2 Distearoyl-sn-glycero-3-ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleyl-phosphatidyl-choline (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dilauroyl phosphatidic acid (DLPA), dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dilauroyl-phosphatidylethanolamine (DLPE), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine, dilauroyl-phosphatidyl-serine (DLPS), dimyristoyl phosphatidylserine (DMPS), diarachidoyl-phosphatidyl-serine (DAPS), dipalmitoyl phosphatidylserine (DPPS), distearoylphosphatidylserine (DSPS), dioleoylphosphatidylserine (DOPS), dipalmitoyl sphingomyelin (DPSP), distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS, DPPE, DSPE, DMPE, DAPE, Ethyl-DSPC and mixtures thereof. Most preferred are DSPG, DSPS, DSPE, DSPC, DAPC and mixtures thereof. Mixtures of phospholipids can also be used, such as, for instance, mixtures of DPPE and/or DSPE (including pegylated derivates), DPPC, DSPC and/or DAPC with DSPS, DPPS, DSPA, DPPA, DSPG, DPPG, Ethyl-DSPC and/or Ethyl-DPPC.

According to a preferred embodiment the formulation comprises at least DSPC, preferably in combination with DSPE-PEG2000 or DPPE-PEG5000.

Other Amphiphilic Materials

The composition forming the stabilizing layer of the gas-filled microvesicles may optionally comprise further amphiphilic components which may also contribute to the formation of the stabilizing layer such as, for instance, fatty acids such as lauric acid, myristic acid, palmitic acid, stearic acid, arachidic acid, behenic acid, oleic acid, linoleic acid and linolenic acid, preferably saturated fatty acids such as myristic acid, palmitic acid, stearic acid and arachidic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate; saponins including sarsasapogenin, smilagenin, hederagenin, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxy)-1-thio-β-D-mannopyranoside; 1,2-dioleyl-sn-glycerol; 1,2-dipalmitoyl-sn-3-succinylglycerol; 1,3-dipalmitoyl-2-succinylglycerol; palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

These further amphiphilic compounds, if present, may be present in variable amounts, for instance up to 25% by moles of the composition forming the stabilizing layer, preferably up to 20%.

According to a preferred embodiment, the formulation for preparing the gas-filled microvesicles comprises at least one fatty acid, preferably palmitic acid, in combination with a phospholipid as above defined, preferably DSPC and DPPE-PEG5000, more preferably in a respective ratio of from 5% (molar ratio) to 20%.

Targeting Ligand

The targeting ligand is a peptide comprising an amino acid sequence selected from AGPTWCEDDWYYCWLFGTGGGK (SEQ ID NO: 01) or VCWEDSWGGEVCFRYDPGGGK (SEQ ID NO: 02).

More preferably, said peptide is a dimer peptide of formula I

The targeting peptide is preferably conjugated with a phospholipid, preferably a pegylated phospholipid and even more preferably DSPE-PEG. Preferably, said targeting peptide is a lipopeptide of formula II. The amount of lipopeptide in the formulation is preferably from 0.1% to 5% by molar ratio with respect to all lipids (phospholipid+fatty acid), more preferably from 0.2% to 1%.

Details on the preparation of the monomeric peptides, of the dimeric peptide and of the lipopeptide are illustrated in WO 2007/067979, herein incorporated by reference.

Histidine

Histidine, preferably L-histidine, can be added either to the dry formulation to be reconstituted or to the carbohydrate solution for reconstitution. Preferably histidine is added to the formulation to be lyophilized; this allows the use of conventional redispersing carbohydrate solutions The amount of histidine shall preferably be such that the concentration of histidine in the aqueous suspension of gas-filled microvesicles for injection is from 1.5 mM to 20 mM, preferably from 2.5 mM to 10 mM and even more preferably from 3 mM to 8 mM.

Aqueous Carrier

The aqueous carrier for preparing the suspension of gas-filled microvesicles is a carbohydrate-containing aqueous solution, preferably iso-osmolar. Preferably the carbohydrate is glucose. The concentration of the carbohydrate in the suspension is preferably from 2% to 20% (w/w), more preferably of from 3% to 15%. Particularly for glucose, the concentration in the final suspension is preferably from 3% to 8%, more preferably from 4 to 6%.

Preparation of Microvesicles

The microvesicles according to the invention can be manufactured according to any known method in the art. Typically, the manufacturing method involves the preparation of a dried powdered material comprising the composition of the invention, preferably by lyophilization (freeze drying) of an aqueous or organic suspension comprising said composition. The microvesicles can then be obtained by reconstitution of the lyophilized preparation in an aqueous carrier, upon gentle agitation in the presence of a gas.

Preferably, as disclosed for instance in International patent application WO2004/069284, a composition comprising the mixture of phospholipids and fatty acids can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation, preferably in admixture with a lyoprotecting agent (such as those previously listed, in particular carbohydrates, sugar alcohols, polyglycols, polyoxyalkylene glycols and mixtures thereof). The emulsion can be obtained by submitting the aqueous medium and the solvent in the presence of the phospholipids and fatty acids to any appropriate emulsion-generating technique known in the art, such as, for instance, sonication, shaking, high pressure homogenization, micromixing, membrane emulsification, flow focusing emulsification, high speed stirring or high shear mixing. Preferably, an organic solution containing a phospholipid and a fatty acid is first prepared; separately, a targeting lipopeptide and optionally a pegylated phospholipid are dissolved in an aqueous solution containing a lyoprotective agent and optionally histidine; the organic and aqueous phases are then admixed and emulsified as described above. The so obtained microemulsion may optionally be diluted with a solution containing a lyoprotective agent and optionally histidine. The microemulsion, which contains microdroplets of solvent surrounded and stabilized by phospholipids and fatty acids, is then lyophilized according to conventional techniques to obtain a lyophilized material.

The freeze-dried (or lyophilized) product is generally in the form of a powder or a cake, and can be stored (typically in a vial) in contact with the desired gas. The product is readily reconstitutable in a suitable physiologically acceptable aqueous liquid carrier, such a carbohydrate-containing aqueous solution as discussed above.

Gas

Any biocompatible gas, gas precursor or mixture thereof may be employed to form the microvesicles of the invention (hereinafter also identified as "microvesicle-forming gas").

The gas may comprise, for example, air; nitrogen; oxygen; carbon dioxide; hydrogen; nitrous oxide; a noble or inert gas such as helium, argon, xenon or krypton; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{12}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof. Particularly preferred is $C_4F_{10}$ and even more preferred is a mixture of nitrogen with $C_4F_{10}$, preferably in a 35/65 v/v ratio.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

Pharmaceutical Kit and Administration

Microvesicles suspensions according to the invention can be stored as such or preferably in form of freeze dried precursor which can be reconstituted with an aqueous carrier. According to the invention, the precursor of the microvesicles suspension is thus preferably stored in dried powdered form and as such can advantageously be packaged in a two component diagnostic and/or therapeutic kit, preferably for administration by injection. The kit preferably comprises a first container, containing the lyophilized precursor composition in contact with a selected microvesicle-forming gas and a second container, containing a physiologically acceptable aqueous carrier for reconstituting the suspension of microvesicles, in particular a carbohydrate solution as discussed above, preferably a 5% (w/w) glucose solution. Said two component kit can include two separate containers or a dual-chamber container. In the former case the container is preferably a conventional septum-sealed vial, wherein the vial containing the lyophilized residue is sealed with a septum through which the carrier liquid may be injected using an optionally prefilled syringe. In such a case the syringe used as the container of the second component is also used then for injecting the contrast agent. In the latter case, the dual-chamber container is preferably a dual-chamber syringe and once the lyophilisate has been reconstituted and then suitably mixed or gently shaken, the container can be used directly for injecting the contrast agent.

According to a preferred embodiment, an effective amount of targeted microvesicles is administered to a patient, typically by injection of a suspension thereof. The imaging of the region of interest (allegedly comprising a tissue expressing KDR-receptors) will thus be enhanced by the presence of the microvesicles bound to the receptor (if any) in the region of interest.

The microvesicles suspension of the present invention can be used in a variety of diagnostic and/or therapeutic techniques, including in particular contrast enhanced ultrasound imaging.

Examples of imaging techniques which may be employed in ultrasound applications include, for example, fundamental and non-linear (e.g. harmonic) B-mode imaging, pulse or phase inversion imaging and fundamental and non-linear Doppler imaging; if desired three- or four-dimensional imaging techniques may be used. Furthermore, diagnostic techniques entailing the destruction of gas-filled microvesicles (e.g. by means of ultrasound waves at high acoustical pressure) which are highly sensitive detection methods are also contemplated.

Typically, once the subject (e.g. a mammal) undergoing the desired ultrasound imaging technique has been administered with an effective amount of the microvesicles suspension, a selected region of interest is submitted to ultrasound irradiation and the resulting echo signal is collected. The collected signal may thus be used, for instance, for displaying a contrast enhanced image of the region of interest; alternatively the signal may be used for computing parametric maps of the region of interest.

Microvesicles suspension according to the invention can typically be administered, preferably via iv injection, in a concentration of from about 0.01 to about 1.0 μL of gas per kg of patient, depending e.g. on their respective composition, the tissue or organ to be imaged and/or the chosen imaging technique. This general concentration range can of course vary depending on specific imaging applications, e.g. when signals can be observed at very low doses such as in colour Doppler or power pulse inversion.

The following examples will help to further illustrate the invention.

EXAMPLES

Materials and Methods

The following materials are employed in the subsequent examples:

| | |
|---|---|
| DSPC | 1,2-Distearoyl-SN-glycero-3-Phosphocholine (Genzyme pharmaceuticals) |
| Palmitic Acid | Hexadecanoic acid (Fluka) |
| DSPE-PEG 2000 | 1,2-Distearoyl-SN-glycero-3-phosphoethanolamine-N-[Methoxy(Polyethylene glycol)-2000)] (Genzyme pharmaceuticals) |
| DPPE-PEG 5000 | 1,2-Dipalmitoyl-SN-glycero-3-phosphoethanolamine-N-[Methoxy(Polyethylene glycol)-5000)] (Genzyme pharmaceuticals) |
| PEG4000 | Polyethyleneglycol (MW = 4000) (Fluka) |
| Cyclooctane | (Fluka) |
| Bicarbonate | Sodium hydrogenocarbonate (Fluka) |
| $Na_2HPO_4$ | di-sodium hydrogen phosphate dodecahydrate (Fluka) |
| $NaH_2PO_4$ | Sodium dihydrogen phosphate (Fluka) |
| Tris | Trizma base (Fluka) |
| Histidine | L-Histidine (Fluka) |

Size distributions concentrations of microvesicles in the suspension were measured by means of a Coulter counter (Multisizer 3) fitted with a 30 μm aperture (dilution: 50 μL in 100 mL NaCl 0.9% solution); pH values were measured using a MP230 pH meter (Mettler Toledo) fitted with an Inlab 410 electrode (Mettler Toledo).

Example 1

Preparation of Lyophilized Precursors of Gas-Filled Microvesicles without pH-Adjusting Additives
Preparation of Lipopeptide of Formula II The lipopeptide of formula II was prepared as described in detail in the working examples of PCT patent application WO 2007/067979, herein incorporated by reference. Briefly, as explained in more detail in the above PCT application, peptide AGPTWCEDDWYYCWLFGTGGGK (SEQ ID NO: 01) was synthesized by solid phase peptide synthesis (SPPS) using Fmoc-protected amino acids. The N-terminus was acetylated and Fmoc-Lys (ivDde)-OH (Nα-Fmoc-Nε-[1-(4,4-dimethyl-2,6-dioxocyclohex-1-ylidene)-3-methylbutyl]-lysine) was coupled to the side chain of $Lys^{22}$. After Fmoc deprotection, cleavage from the resin and cleavage of the other protecting groups (with the exception of ivDde group), peptide was cyclized (formation of disulfide bridge). The cyclized peptide was purified by preparative HPLC and lyophilized.

Peptide VCWEDSWGGEVCFRYDPGGGK (SEQ ID NO: 02) was also synthesized by SPPS using Fmoc-protected amino acids. The N-terminus was acetylated and two sequential coupling of Fmoc-Adoa-OH (8-(Fmoc-amino)-3,6-dioxa-octanoic acid) were carried out to the side chain of $Lys^{21}$. After Fmoc deprotection, cleavage from the resin and cleavage of the other protecting groups, peptide was cyclized (formation of disulfide bridge). The cyclized peptide was purified by preparative HPLC and lyophilized.

Preparation of the dimeric peptide (Formula I): Disuccinimidyl glutarate (DSG) was coupled to the α-amino function of the lysine linked to the 8-amino function of $Lys^{22}$ of the peptide (SEQ ID NO. 01). After purification, the product was then reacted with the amino function of the Adoa moiety linked to the Lys21 of the peptide (SEQ ID NO: 02). The crude heterodimer was purified by preparative HPLC and lyophilized. The remaining ivDde-protecting group was then cleaved and the final product was again purified by preparative HPLC and the acetate salt was formed by ion exchange. The product solution was lyophilized to yield dimeric peptide (formula I).

Preparation of the lipopeptide (formula II): Disuccinimidyl glutarate (DSG) was coupled to the previously synthesized dimeric peptide (formula I). After purification, the product was reacted with DSPE-PEG2000-amine. The product was purified by preparative HPLC and lyophilized.

Prep-01

A lyophilized precursor for preparing a suspension of gas-filled microvesicles was prepared as follows:

(i) 60 mg of a lipid mixture (DSPC and palmitic acid, in a molar ratio of 80/20) were dissolved in cyclooctane (4.8 ml) at 70° C.

(ii) Separately, DSPE-PEG 2000 (3% w/w) and the lipopeptide of formula II (0.2% w/w) were dispersed in 1 ml of a Tris buffer 20 mM (pH 7.6); the dispersion was then admixed with 60 ml of a 10% PEG4000 solution.

(iii) The cyclooctane preparation (i) was emulsified in the PEG4000 aqueous solution (ii) using an in-line high speed homogenizer (Megatron MT3000) for 5 min at 12,000 rpm.

(iv) The resulting emulsion was heated at 80° C. for 1 hour under agitation. After cooling to room temperature (~1 hour), (v) The emulsion was diluted four times with 10% PEG4000 aqueous solution and sampled in volumes of 1 ml in DIN8R vials.

(vi) The vials were inserted into a lyophilizator (TELSTAR Lyobeta-35 freeze dryer), cooled to −50° C. for 2 hours and then freeze-dried at −25° C. and 0.2 mBar during 12 hours, with a final drying step at 30° C. and 0.1 mBar for further 6 hours.

A 35/65 (by volume) mixture of $C_4F_{10}$/N2 was added to the headspace of the vials, which were then stoppered and sealed.

Prep-02 to Prep-05

The preparation of Prep-01 above was repeated with various molar ratio of DSPC/Palmitic acid in the organic phase (see Table 1) and with the difference that the amounts of DSPE-PEG 2000 or DPPE-PEG 5000 and of the lipopeptide of formula II were modified in the preparation of the aqueous solution of step (ii), as illustrated in Table 1. Furthermore, Prep-03 and Prep-05 were diluted twice (instead of four times) in step (v) and then sampled in volumes of 1.5 ml in DIN8R vials.

Table 1 below summarizes the differences in the various preparations of lyophilized precursors.

TABLE 1

Preparation of lyophilized precursors

|  | DSPC/PA molar ratio | DSPE-PEG2000 (molar %) | DPPE-PEG5000 (molar %) | Lipopeptide (molar %) | Dilution of emulsion (ml in vial) |
|---|---|---|---|---|---|
| Prep-01 | 80/20 | 3% | — | 0.2% | 4x (1.0 ml) |
| Prep-02 | 95/5 | — | 0.5% | 0.5% | 4x (1.0 ml) |
| Prep-03 | 95/5 | — | 0.5% | 0.5% | 2x (1.5 ml) |
| Prep-04 | 80/20 | — | — | 0.8% | 4X(1.0 ml) |
| Prep-05 | 80/20 | — | — | 0.8% | 2X(1.5 ml) |

Example 2

Effect of the pH of Dispersing Saccharide Solutions on Microvesicles Aggregation Preparations obtained according Example 1 were redispersed in 1 ml of water or of various solutions of 5% (w/w) glucose at different pH values, namely 3.5, 3.8 and 6.5.

To obtain a glucose 5% solution with a pH of 6.5, 30 to 34 µL of NaOH 0.1 N were added in 20 mL of glucose 5% solution (→0.15 to 0.17 mM NaOH). To obtain a glucose 5% solution with a pH of 3.5, 32 to 40 µL of HCl 0.1 N were added in 20 mL glucose 5% solution The suspension obtained are identified as Susp-01 to Susp-05 (from respective preparations Prep-01 to Prep-05, with the suffixes a to d identifying the reconstitution with (a) distilled water (control), (b) glucose solution pH 3.5, (c) glucose solution pH 3.8 and (d) glucose solution pH 6.5, respectively. Thus, for instance, Susp.02c identifies a suspension of microvesicles obtained by dispersing Prep.02 above in 1 ml of 5% glucose at pH 3.8.

The obtained suspensions of gas-filled microvesicles were characterized with Coulter counter to determine the microvesicles concentration and the mean particle size by number ($D_N$) of microvesicles in the suspensions. The results are illustrated in Table 2 and Table 3, respectively (in these and in the following tables, the values indicate either the actual value referred to a single suspension or to an average value in case of multiple preparations of the same suspension). The pH of the prepared suspension was also measured and is reported in the following table 4.

TABLE 2 concentration of microvesicles upon reconstitution with different solutions

| | Number of microvesicles ($10^9$ particles/ml) measured on suspensions obtained upon reconstitution with solution: | | | |
|---|---|---|---|---|
| | (a)* | (b) | (c) | (d) |
| Susp-01 | 3.61 | 1.25 | 2.66 | 3.92 |
| Susp-02 | 2.58 | 0.55 | 1.32 | 2.76 |
| Susp-03 | 2.68 | 0.25 | 0.34 | 2.26 |
| Susp-04 | 2.29 | 0.22 | 0.73 | 2.69 |
| Susp-05 | 3.27 | 0.07 | 0.10 | 3.22 |

*= control

TABLE 3

$D_N$ of microvesicles suspensions upon reconstitution with different solutions

| | $D_N$ (µm) of microvesicles measured on suspensions obtained upon reconstitution with solution: | | | |
|---|---|---|---|---|
| | (a)* | (b) | (c) | (d) |
| Susp-01 | 1.29 | 1.76 | 1.38 | 1.29 |
| Susp-02 | 1.38 | 2.36 | 1.64 | 1.35 |
| Susp-03 | 1.50 | 4.05 | 3.48 | 1.56 |
| Susp-04 | 1.38 | 2.40 | 1.59 | 1.33 |
| Susp-05 | 1.40 | 5.22 | 4.84 | 1.39 |

*= control

TABLE 4 pH of microvesicles suspensions upon reconstitution with different solutions

| | pH of the suspension after reconstitution with | | | |
|---|---|---|---|---|
| | (a)* | (b) | (c) | (d) |
| Susp.01 | 7.6 | 4.7 | 6.0 | 7.3 |
| Susp.02 | 7.6 | 5.0 | 6.4 | 7.3 |
| Susp.03 | 6.9 | 4.6 | 4.8 | 7.0 |
| Susp.04 | n.d. | 4.7 | 5.2 | 7.1 |
| Susp.05 | 7.5 | 4.4 | 5.1 | 7.3 |

*= control

As inferable from the values in the table 2, the concentration of microvesicles in the obtained suspension substantially decreases with respect to control when glucose solution at pH of 3.5 or 3.9 (columns b and c) are employed for the reconstitution of the freeze-dried preparations, while when glucose solution at pH 6.5 (col. d) is used the concentration is substantially similar to control (col. a).

As inferable from table 3, reconstitution of the lyophilized preparations with low pH glucose solutions provide an undesirable increase in the $D_N$ value of the microvesicles.

Example 3

Effect on microvesicles aggregation of various pH-adjusting agents in the reconstitution of Prep-01 with saccharide solutions at different pH values Example 3a: Sodium Bicarbonate The preparation of Prep-01 lyophilized precursor was repeated according to the procedure of Example 1, with the difference that various amounts of sodium bicarbonate were added to the 10% PEG4000 solution used for diluting the emulsion in step (v), to obtain respective lyophilized precursor preparations with different amounts of sodium bicarbonate incorporated therein. The amounts of bicarbonate added to the PEG4000 solution were such to obtain a concentration of bicarbonate in the emulsion of step (v) of 0.125, 0.31, 0.38, 0.80, 1.20 and 2.0 mM, respectively.

The obtained preparations were then redispersed in 1 ml of water or of various solutions of 5% (w/w) glucose at different pH values according to the procedure of Example 2.

Table 5 shows the concentration of microvesicles measured in the various suspensions obtained from respective preparations containing different amounts of sodium bicarbonate.

TABLE 5

Microvesicles concentration in suspensions with sodium bicarbonate

| | \multicolumn{6}{c}{$10^9$ particles/ml in the suspension (concentration of bicarbonate - mM - in emulsion before dilution)} | | | | | |
|---|---|---|---|---|---|---|
| Susp- | — | 0.125 | 0.31 | 0.38 | 0.80 | 1.25 | 2.0 |
| 01(a) | 3.61* | 3.28 | 3.50 | 3.82 | 3.52 | 3.55 | 3.71 |
| 01(b) | 1.25 | 1.34 | 1.81 | 3.61 | 3.90 | 3.56 | 4.04 |
| 01(c) | 2.66 | 2.71 | 3.43 | 3.89 | 3.58 | 3.49 | 4.08 |
| 01(d) | 3.92 | 3.73 | 4.03 | 3.95 | — | 3.64 | 4.24 |

*= control

As inferable from the data illustrated in above table, concentrations of sodium bicarbonate of at least 0.38 mM in the diluted emulsion are advisable, in order to obtain an acceptable concentration of microbubbles over the whole range of pH of the glucose solution used for the reconstitution. On the other side, lower concentrations of bicarbonate may provide suspensions with undesirably lower concentration of microvesicles, particularly when the freeze-dried precursor is reconstituted with a glucose solution at pH of 3.5.

Table 6 shows the pH values measured on the suspensions of table 5.

TABLE 6 pH values of suspensions of microvesicles with sodium bicarbonate

| | \multicolumn{6}{c}{pH value in the suspension (concentration of bicarbonate - mM - in emulsion before dilution)} | | | | | |
|---|---|---|---|---|---|---|
| Susp- | — | 0.125 | 0.31 | 0.38 | 0.80 | 1.25 | 2.0 |
| 01(a) | 7.6* | — | — | — | 8.1 | 9.4 | 9.5 |
| 01(b) | 4.7 | 5.1 | 5.4 | 6.0 | 6.8 | 7.8 | 8.2 |
| 01(c) | 6.0 | 5.5 | 5.8 | 7.6 | 8.1 | 8.5 | 8.6 |
| 01(d) | 7.3 | 7.3 | 7.6 | 8.2 | — | 9.0 | 9.2 |

*= control

As known in the art, the pH of intravenously injectable pH-adjusted solutions should preferably be within a pH range of from about 6 to about 8.5, preferably between about 7 and about 8. As inferable from table 6, when the glucose solution for reconstitution is at the higher end of the pH range (solution d, pH=6.5), relatively low concentrations of bicarbonate may already increase the pH of the final suspension of microvesicles above acceptable values for injection. Thus, by reading tables 5 and 6 in combination, it appears that relatively high concentrations of sodium bicarbonate (which are necessary for providing the desired concentration of microvesicles in glucose solution at relatively low pH) may excessively increase the pH of the injectable solution. On the other side, relatively low concentrations of bicarbonate may not provide the desired concentration of microvesicles in the reconstituted suspension (particularly when using low pH glucose solutions).

Ex. 3b: Tris/HCl Buffer

Example 3a was repeated with the difference the sodium bicarbonate was replaced by Tris/HCl buffer solution (pH=8.0), prepared by dissolving Tris base (121.1 g-1 mole) in distilled water (750 mL), adding HCl (about 40 ml) and then completing the volume to 1 L with distilled water. The volumes of the Tris/Hcl buffer solution added to the PEG4000 solution were such to obtain a concentration of Tris/HCl in the emulsion of step (v) of 0.125, 2.5, 5.0, 10.0 mM, respectively.

Table 7 shows the concentration of microvesicles measured in the various suspensions obtained from respective preparations containing different amounts of Tris/HCl buffer.

TABLE 7

Microvesicles concentration in suspensions with Tris/HCl buffer (pH = 8.0)

| | \multicolumn{4}{c}{Particles($10^9$)/ml in the suspension (concentration of Tris/HCl - mM - in emulsion before dilution)} | | | |
|---|---|---|---|---|
| Susp- | — | 1.25 | 2.5 | 5.0 | 10.0 |
| 01(a) | 3.61* | 2.96 | 2.77 | 2.23 | 1.71 |
| 01(b) | 1.25 | 2.68 | 2.62 | 2.16 | 1.79 |
| 01(c) | 2.66 | 3.02 | 2.56 | 2.24 | 1.82 |
| 01(d) | 3.92 | 3.09 | N.D. | 2.29 | 1.91 |

*= control

As inferable from the data in the above table, reconstitution of preparations containing Tris/HCl buffer provide relatively lower concentrations of microvesicles in the suspension (as compared with control), in particular when the preparation is reconstituted with low pH glucose solutions. An important decrease of microbubble concentration was in particular observed when high concentrations of Tris/HCl buffer were used, particularly 5.0 mM or higher. For this reason, the 2.5 mM Tris/HCl buffer was selected as comparative pH-adjusting agent in subsequent experiments.

Ex. 3c: Phosphate Buffer

Example 3a was repeated with the difference the sodium bicarbonate was replaced by phosphate buffer (pH=7.6) prepared by admixing 43.5 mL of a $Na_2HPO_4$ solution (0.2 M) with 6.5 mL $NaH_2PO_4$ solution (0.2 M). The volumes of the phosphate buffer solution added to the PEG4000 solution were such to obtain a concentration of phosphate in the emulsion of step (v) of 2.5, 5.0 and 10.0 mM, respectively.

Table 8 and Table 9 show the concentration of microvesicles and the $D_N$ values, respectively, measured in the various suspensions obtained from respective preparations containing different amounts of phosphate buffer.

TABLE 8

Microvesicles concentration in suspensions with phosphate buffer (pH = 7.6)

| | \multicolumn{3}{c}{Particles($10^9$)/ml in the suspension (concentration of phosphate - mM - in emulsion before dilution)} | | |
|---|---|---|---|---|
| Susp- | — | 2.5 | 5.0 | 10.0 |
| 01(a) | 3.61* | 3.26 | 3.04 | 2.38 |
| 01(b) | 1.25 | 3.30 | 2.89 | 2.32 |
| 01(c) | 2.66 | 3.24 | 3.08 | 2.40 |
| 01(d) | 3.92 | 3.42 | 2.93 | 1.84 |

*= control

As for example 3b, reconstitution of preparations containing phosphate buffer provide relatively lower concentrations of microvesicles in the suspension (as compared with control), in particular when the preparation is reconstituted with low pH glucose solutions. An important decrease of microbubble concentration was in particular observed when higher concentrations of phosphate buffer were used. For this reason, the 2.5 mM phosphate buffer was selected as comparative pH-adjusting agent in subsequent experiments.

TABLE 9

$D_N$ values of microvesicles is suspensions with phosphate buffer (pH = 7.6)

$D_N$ (μm) in the suspension (concentration of phosphate - mM - in emulsion before dilution

| Susp- | — | 2.5 | 5.0 | 10.0 |
|---|---|---|---|---|
| 01(a) | 1.28* | 1.31 | 1.35 | 1.50 |
| 01(b) | 1.76 | 1.32 | 1.38 | 1.50 |
| 01(c) | 1.38 | 1.32 | 1.36 | 1.44 |
| 01(d) | 1.28 | 1.30 | 1.38 | 1.66 |

*= control

As observable from the above table, $D_N$ values of the microvesicles suspensions are slightly higher than those of the control, particularly for preparations reconstituted with low pH glucose solutions and at higher concentrations of phosphate buffer.

Ex. 3d: Histidine

Example 3a was repeated with the difference that sodium bicarbonate was replaced by histidine. The amounts of histidine added to the PEG4000 solution were such to obtain a concentration of histidine in the emulsion of step (v) of 2.5, 5.0 and 10.0 mM, respectively.

Table 10 shows the concentration of microvesicles and Table 11 the $D_N$ values measured in the various suspensions obtained from respective preparations containing different amounts of histidine. The concentration of histidine in the final suspension of microvesicles was of 2.5, 5.0 and 10.0 mM, respectively.

TABLE 10

Microvesicles concentration in suspensions with histidine at different concentrations Particles($10^9$)/ml in the suspension (concentration of histidine - mM - in emulsion before dilution)

| Susp- | — | 2.5 | 5.0 | 10.0 |
|---|---|---|---|---|
| 01(a) | 3.61* | 3.49 | 3.37 | 3.51 |
| 01(b) | 1.25 | 3.29 | 3.35 | 3.52 |
| 01(c) | 2.66 | 3.36 | 3.22 | 3.54 |
| 01(d) | 3.92 | 3.48 | 3.48 | — |

*= control

TABLE 11

$D_N$ of microvesicles is suspensions with histidine at different concentrations $D_N$ (μm) in the suspension (concentration of histidine - mM - in emulsion before dilution)

| Susp- | — | 2.5 | 5.0 | 10.0 |
|---|---|---|---|---|
| 01(a) | 1.28* | 1.22 | 1.22 | 1.20 |
| 01(b) | 1.76 | 1.25 | 1.22 | 1.21 |
| 01(c) | 1.38 | 1.24 | 1.22 | 1.22 |
| 01(d) | 1.28 | 1.24 | 1.20 | ND |

*= control

As observable from the above table, $D_N$ values of the microvesicles suspensions with histidine are comparable or slightly lower than those of the control, indicating that microvesicles in the histidine-containing suspensions have a comparable sizes than those in the control whatever the pH of the glucose solution and the concentration of the histidine.

Example 4

Effect on Microvesicles Aggregation of Various pH-Adjusting Agents in the Reconstitution of Prep-02 with Saccharide Solutions at Different pH Values Example 4a: Microvesicles Suspension with Comparative pH Adjusting Agents The preparation of Prep-02 lyophilized precursor was repeated according to the procedure of Example 1, with the difference that sodium bicarbonate, Tris/HCl buffer or phosphate buffer were added to the 10% PEG4000 solution used for dilution of the emulsion in the step v, to obtain respective lyophilized precursor preparations. The amounts of pH-adjusting agent added to the PEG4000 solution were such to obtain an optimized concentration (as determined in example 3) of the respective pH-adjusting agent in the diluted emulsion as indicated in tables 12 and 13.

The obtained preparations were then redispersed in 1 ml of water or of the various 5% (w/w) glucose solutions at different pH values according to the procedure of Example 2.

Tables 12 and 13 show the concentration of microvesicles and the $D_N$ values measured in the various suspensions obtained from respective preparations containing the selected pH-adjusting agent.

TABLE 12

Microvesicles concentration in suspensions with different pH-adjusting agents $10^9$ particles/ml in the suspension (concentration of pH-adjuster in emulsion before dilution)

| Susp- | — | NaHCO$_3$ 0.5 mM | Tris/HCl 2.5 mM | Phosphate 2.5 mM |
|---|---|---|---|---|
| 02(a) | 2.58* | 2.89 | 1.79 | 1.89 |
| 02(b) | 0.55 | 2.17 | 1.65 | 1.61 |
| 02(c) | 1.32 | 2.71 | 1.62 | 1.64 |
| 02(d) | 2.76 | 2.63 | 1.50 | 1.75 |

*= control

TABLE 13

$D_N$ value of microvesicles in suspensions with different pH-adjusting agents

Dn values of microvesicles in the suspension (concentration of pH-adjuster in emulsion before dilution)

| Susp- | — | NaHCO$_3$ 0.5 mM | Tris/HCl 2.5 mM | Phosphate 2.5 mM |
|---|---|---|---|---|
| 02(a) | 1.38* | 1.36 | 1.52 | 1.52 |
| 02(b) | 2.36 | 1.48 | 1.57 | 1.57 |
| 02(c) | 1.64 | 1.38 | 1.54 | 1.55 |
| 02(d) | 1.35 | 1.39 | 1.58 | 1.53 |

*= control

As inferable from the data illustrated in tables 12 and 13, the number of particles in suspensions with different conventional pH-adjusting agents is generally lower than the control, particularly for reconstitution with low pH glucose solutions—02(b)—while the $D_N$ value is generally higher.

Example 4b: Microvesicles Suspension with Histidine

Example 4a was repeated with the difference that the comparative pH-adjusting agents were replaced by histidine at different concentrations, as illustrated in tables 14 and 15. Also in this case the concentration of histidine in the final suspension of microvesicles was of 2.5 mM, 5.0 mM and 10 mM, respectively.

TABLE 14

Microvesicles concentration in suspensions with histidine $10^9$ particles/ml in the suspension (concentration of histidine in emulsion before dilution)

| Susp- | — | 2.5 mM | 5 mM | 10 mM |
|---|---|---|---|---|
| 02(a) | 2.58* | 2.50 | 2.49 | 2.53 |
| 02(b) | 0.55 | 2.16 | 2.43 | 2.06 |
| 02(c) | 1.32 | 2.42 | 2.58 | 2.48 |
| 02(d) | 2.76 | 2.34 | 2.61 | 2.57 |

*= control

TABLE 15

$D_N$ value of microvesicles in suspensions with histidine $D_N$ values of microvesicles in the suspension (concentration of histidine in emulsion before dilution)

| Susp- | — | 2.5 mM | 5 mM | 10 mM |
|---|---|---|---|---|
| 02(a) | 1.38* | 1.33 | 1.35 | 1.32 |
| 02(b) | 2.36 | 1.38 | 1.37 | 1.39 |
| 02(c) | 1.64 | 1.35 | 1.32 | 1.33 |
| 02(d) | 1.35 | 1.36 | 1.34 | 1.32 |

*= control

As inferable from the data illustrated in tables 14 and 15, the number of particles and the $D_N$ values of microvesicles measured in suspensions with histidine are generally comparable to those measured on the control solution, at any pH of the glucose reconstituting solution and at any concentration of histidine.

Example 5

Effect on Microvesicles Aggregation of Phosphate Buffer and Histidine in the Reconstitution of Prep-03 with Saccharide Solutions at Different pH Values The preparation of Prep-03 lyophilized precursor was repeated according to the procedure of Example 1, with the difference that phosphate buffer or histidine were added to the 10% PEG4000 solution used for emulsion dilution (step v) to obtain respective lyophilized precursor preparations. The amounts of phosphate or of histidine added to the PEG4000 solution were such to obtain a 2.5 mM concentration of phosphate and concentrations of 5 mM, 10 mM and 20 mM of histidine in the diluted emulsion of step (v), as indicated in tables 16 and 17, corresponding to a concentration of histidine in the final suspension of microvesicles of about 3.75 mM, 7.5 mM and 15 mM.

The obtained preparations were then redispersed in 2 ml of the various 5% (w/w) glucose solutions at different pH values according to the procedure of Example 2.

Tables 16 and 17 show the concentration and the $D_N$ values in the various suspensions with respective preparations containing the selected pH-adjusting agent.

TABLE 16

Microvesicles concentration in suspensions $10^9$ particles/ml in the suspension (concentration of pH-adjusting agent in emulsion before dilution)

| Susp- | Phosphate 2.5 mM | Hist 5.0 mM | Hist 10 mM | Hist 20 mM |
|---|---|---|---|---|
| 03(a) | 1.09 | 2.51 | 2.59 | 2.86 |
| 03(b) | 0.72 | 2.08 | 2.55 | 2.32 |
| 03(c) | 0.92 | 2.37 | 2.55 | 2.62 |
| 03(d) | 0.90 | 2.23 | 2.54 | 2.70 |

TABLE 17

$D_N$ value of microvesicles in suspensions with different pH-adjusters $D_N$ value (concentration of pH-adjusting agent in emulsion before dilution)

| Susp- | Phosphate 2.5 mM | Hist 5.0 mM | Hist 10 mM | Hist 20 mM |
|---|---|---|---|---|
| 03(a) | 1.93 | 1.50 | 1.47 | 1.43 |
| 03(b) | 2.14 | 1.56 | 1.48 | 1.52 |
| 03(c) | 1.97 | 1.51 | 1.47 | 1.48 |
| 03(d) | 2.04 | 1.55 | 1.48 | 1.47 |

As inferable from the data in table 16, the number of particles of microvesicles measured in suspensions with histidine at different concentrations are generally higher than the number measured in the comparative phosphate buffered preparation, particularly at high pH values of the glucose solution and at high concentrations of histidine. As inferable from the data in Table 17, the DN values of microvesicles measured in suspensions with histidine at different concentrations are generally lower than the DN values measured in the comparative phosphate buffered preparation.

Example 6

Effect on Microvesicles Aggregation of Phosphate Buffer and Histidine in the Reconstitution of Prep-04 with Saccharide Solutions at Different pH Values The preparation of Prep-04 lyophilized precursor was repeated according to the procedure of Example 1, with the difference that comparative pH-adjusting agents (i.e. bicarbonate, Tris/HCl or phosphate) or histidine were added to the 10% PEG4000 solution used for emulsion dilution (step v), to obtain respective lyophilized precursor preparations. The amounts of added pH-adjusting agents were such as to obtain the following concentrations in the diluted emulsion, as indicated in tables 18 and 19: 0.38 mM bicarbonate, 2.5 mM Tris/HCl, 2.5 mM phosphate or 2.5 mM histidine.

The obtained preparations were then redispersed in 1 ml of the various 5% (w/w) glucose solutions at different pH values according to the procedure of Example 2.

Tables 18 and 19 show the concentration of microvesicles and the $D_N$ values measured in the various suspensions obtained from respective preparations containing the selected pH-adjusting agent.

TABLE 18

Microvesicles concentration in suspensions $10^9$ particles/ml in the suspension (concentration of pH-adjusting agent in emulsion before dilution)

| Susp- | Bicarbonate (0.38 mM) | Tris/HCl (2.5 mM) | Phosphate (2.5 mM) | Histidine (2.5 mM) |
|---|---|---|---|---|
| 04(a) | 3.70 | 2.26 | 3.10 | 3.11 |
| 04(b) | 1.47 | 2.15 | 2.69 | 2.82 |
| 04(c) | 3.28 | 2.49 | 2.82 | 2.87 |
| 04(d) | 3.65 | 2.41 | 2.77 | 3.07 |

*= control

TABLE 19

$D_N$ value of microvesicles in suspensions with different pH-adjusters $D_N$ value (concentration of pH-adjusting agent in emulsion before dilution)

| Susp- | Bicarbonate (0.38 mM) | Tris/HCl (2.5 mM) | Phosphate (2.5 mM) | Histidine (2.5 mM) |
|---|---|---|---|---|
| 04(a) | 1.32 | 1.36 | 1.38 | 1.29 |
| 04(b) | 1.47 | 1.40 | 1.42 | 1.31 |
| 04(c) | 1.35 | 1.38 | 1.38 | 1.31 |
| 04(d) | 1.33 | 1.40 | 1.39 | 1.30 |

As inferable from the data in table 18, the number of particles in suspensions with different conventional pH-adjusting agents is generally lower than the number measured in the suspension with histidine, particularly in low pH glucose solutions. As inferable from the data in table 19, the DN values of microvesicles in suspensions with different conventional pH-adjusting agent agents is generally higher than the DN value measured in the suspension with histidine, particularly in low pH glucose solutions.

Example 7

Effect on Microvesicles Aggregation of Phosphate Buffer and Histidine in the Reconstitution of Prep-05 with Saccharide Solutions at Different pH Values The preparation of Prep-05 lyophilized precursor was repeated according to the procedure of Example 1, with the difference that phosphate buffer or histidine were added to the 10% PEG4000 solution used for emulsion dilution (step v), to obtain respective lyophilized precursor preparations. The amounts of phosphate or of histiding added to the PEG4000 solution were such to obtain a 2.5 mM concentration of phosphate and concentrations of 2.5 mM, 5 mM or 10 mM of histidine in the diluted emulsion as indicated in tables 20 and 21.

The obtained preparations were then redispersed in 2 ml of water or of the various 5% glucose solutions at different pH values according to the procedure of Example 2.

Tables 20 and 21 show the concentration of microvesicles and the $D_N$ values measured in the various suspensions obtained from respective preparations containing the selected pH-adjusting agent.

TABLE 20

Microvesicles concentration in suspensions $10^9$ particles/ml in the suspension (concentration of pH-adjusting agent in emulsion before dilution)

| Susp- | Phosphate 2.5 mM | Hist. 5 mM | Hist 10 mM |
|---|---|---|---|
| 05(a) | 3.00 | 3.17 | 3.40 |
| 05(b) | 2.68 | 3.00 | 3.16 |
| 05(c) | 2.76 | 3.07 | 3.38 |
| 05(d) | 2.93 | 3.28 | 3.43 |

TABLE 21

$D_N$ value of microvesicles in suspensions $D_N$ value (concentration of pH-adjusting agentin emulsion before dilution)

| Susp- | Phosphate 2.5 mM | Hist. 5 mM | Hist 10 mM |
|---|---|---|---|
| 05(a) | 1.39 | 1.35 | 1.34 |
| 05(b) | 1.42 | 1.37 | 1.36 |
| 05(c) | 1.43 | 1.37 | 1.35 |
| 05(d) | 1.39 | 1.34 | 1.34 |

As inferable from the data illustrated in table 20, the number of particles in suspensions with phosphate buffer is generally lower than the number measured in the suspension with histidine at different concentrations, particularly in low pH glucose solutions. As inferable from the data illustrated in table 21, the $D_N$ values of microvesicles in suspensions with phosphate buffer is generally higher than the $D_N$ value measured in the suspensions with histidine at different concentrations, particularly in low pH glucose solutions.

The invention claimed is:

1. An aqueous suspension of gas-filled microvesicles, said gas-filled microvesicles comprising distearoyl-phosphatidyl-choline (DSPC), palmitic acid, DPPE-PEG5000, and a targeting ligand comprising a peptide having an amino acid sequence selected from AGPTWCEDDWYYCWLFGTGGGK (SEQ ID NO: 01), VCWEDSWGGEVCFRYDPGGGK (SEQ ID NO: 02) or a combination thereof, said aqueous suspension further comprising a carbohydrate and a histidine at a concentration of from 1.5 mM to 20 mM such that the aqueous suspension is compatible with intravenous injection.

2. The aqueous suspension according to claim 1 wherein said targeting ligand is in a form of a dimeric peptide comprising a combination of SEQ ID NO: 01 and SEQ ID NO: 02.

3. The aqueous suspension according to claim 1, wherein said carbohydrate is a glucose.

4. The aqueous suspension according to claim 1, wherein the palmitic acid is present in a molar amount of from 5% to 20%.

5. The aqueous suspension according to claim 1, wherein the peptide is conjugated with a phospholipid to form a lipopeptide.

6. The aqueous suspension according to claim 5, wherein said lipopeptide is present in a molar amount of from 0.1% to 5% by molar ratio with respect to other components of the gas-filled microvesicles.

7. The aqueous suspension according to claim 1, wherein said targeting ligand is a lipopeptide of formula II:

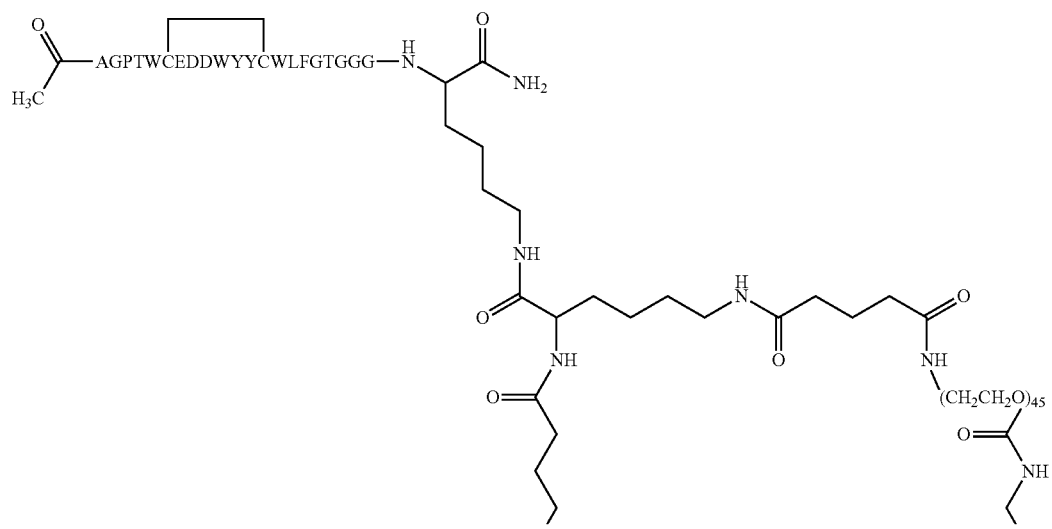
(II)
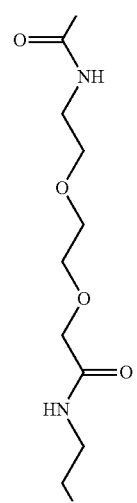
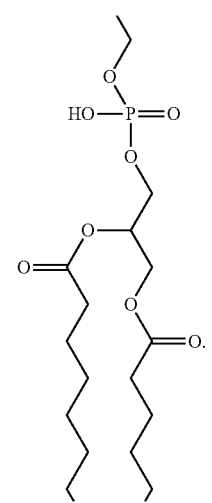

-continued

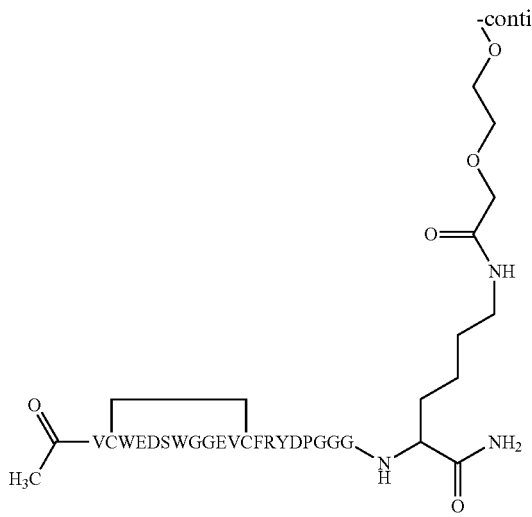 

8. The aqueous suspension according to claim 1, wherein said gas-filled microvesicles comprise a fluorinated physiologically acceptable gas.

9. The aqueous suspension according to claim 1, wherein the concentration of the histidine in the aqueous suspension is from 2.5 mM to 10 mM.

10. A pharmaceutical kit for preparing an injectable aqueous suspension of gas-filled microvesicles comprising:
a first container comprising a physiologically acceptable gas in contact with a freeze-dried formulation comprising (i) distearoyl-phosphatidyl-choline (DSPC), palmitic acid, DPPE-PEG5000, (ii) a targeting ligand comprising a peptide having an amino acid sequence selected from AGPTWCEDDWYYCWLFGTGGGK (SEQ ID NO: 01), VCWEDSWGGEVCFRYDPGGGK (SEQ ID NO: 02) or a combination thereof, and (iii) a histidine; and
a second container comprising a carbohydrate-containing aqueous solution capable of reconstituting the freeze-dried formulation into the injectable aqueous suspension of gas-filled microvesicles such that the concentration of the histidine in the injectable aqueous suspension of gas-filled microvesicles is from 1.5 mM to 20 mM.

11. The pharmaceutical kit according to claim 10, wherein said targeting ligand is in a form of a dimeric peptide comprising a combination of SEQ ID NO: 01 and SEQ ID NO: 02.

12. The pharmaceutical kit according to claim 10, wherein the concentration of the histidine in the injectable aqueous suspension of gas-filled microvesicles is from 2.5 mM to 10 mM.

13. A method of using the pharmaceutical kit according to claim 10 for imaging a region of interest in a subject comprising:
preparing an aqueous suspension of gas-filled microvesicles by combining contents of the first container with the carbohydrate-containing aqueous solution such that the concentration of histidine in the aqueous suspension of gas-filled microvesicles is from 1.5 mM to 20 mM;
administering an effective amount of the aqueous suspension of gas-filled microvesicles to the subject by intravenous injection;
submitting said region of interest to ultrasound irradiation, and
collecting respective echo signals from said region of interest.

14. The pharmaceutical kit according to claim 10, wherein said carbohydrate is a glucose.

15. The pharmaceutical kit according to claim 10, wherein the peptide is conjugated with a phospholipid to form a lipopeptide.

16. The pharmaceutical kit according to claim 10, wherein said targeting ligand is a lipopeptide of formula II:

(II)
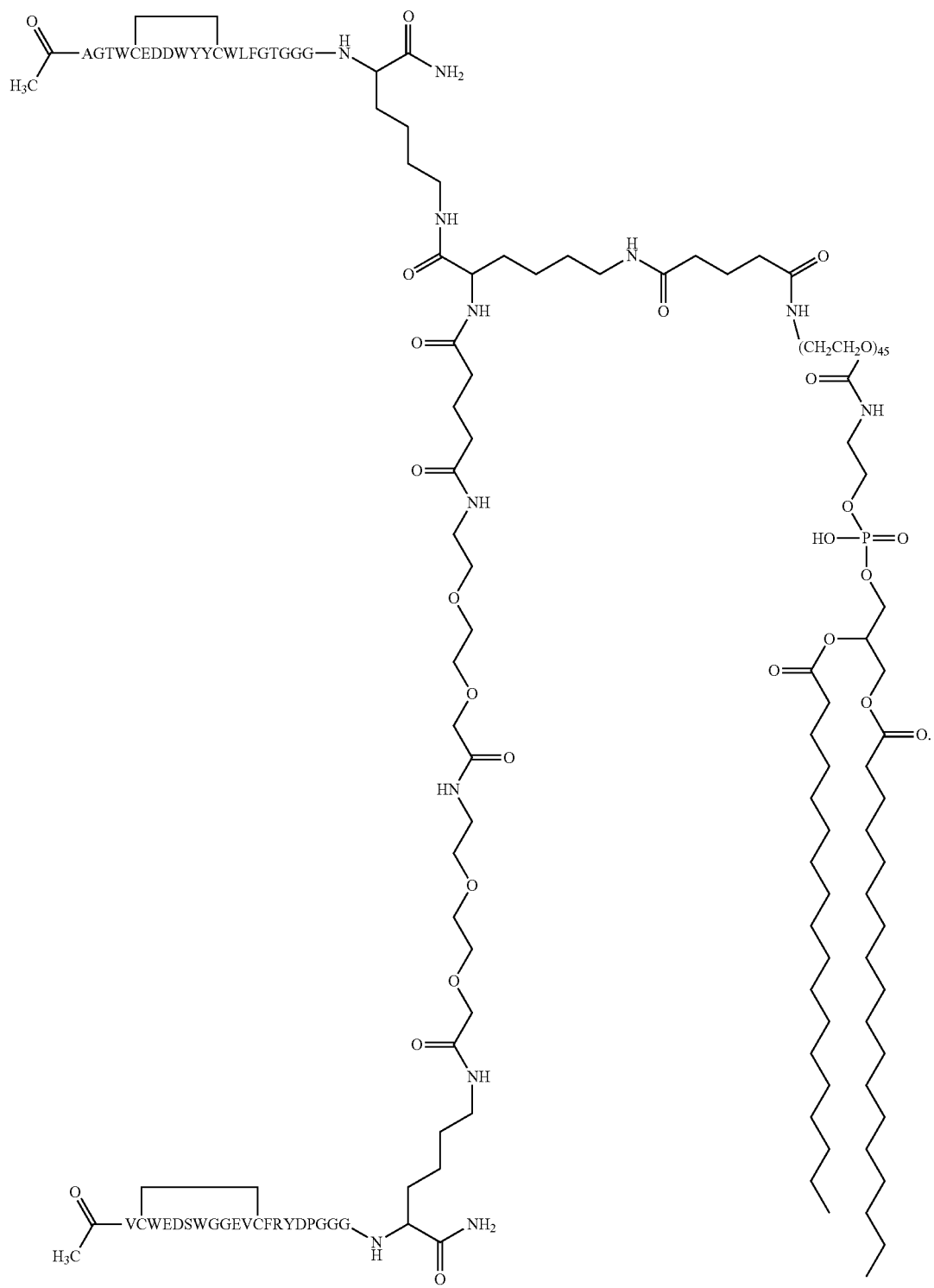
17. The pharmaceutical kit according to claim 10, wherein the physiologically acceptable gas is a fluorinated physiologically acceptable gas.
* * * * *